United States Patent
Nilsson et al.

(10) Patent No.: US 6,251,394 B1
(45) Date of Patent: Jun. 26, 2001

(54) METHOD AND A SYSTEM FOR ENHANCED IN VIVO CLEARANCE OF DIAGNOSTIC AND/OR THERAPEUTIC AGENTS BY EXTRACORPOREAL DEPLETION, AND THE USE OF SAID AGENTS FOR SAID PURPOSE

(75) Inventors: Rune Nilsson; Lars Lindgren, both of Lund; Kristina Norrgren, Åkarp; Bengt Sandberg, Lund; Hans Olof Sjögren, Lund; Sven-Erik Strand, Lund, all of (SE)

(73) Assignee: Mitra Medical Technology AB, Lund (SE)

( * ) Notice: Subject to any disclaimer, the term of this patent is extended or adjusted under 35 U.S.C. 154(b) by 0 days.

(21) Appl. No.: 08/090,047

(22) PCT Filed: Jan. 15, 1992

(86) PCT No.: PCT/SE92/00020

§ 371 Date: Oct. 12, 1993

§ 102(e) Date: Oct. 12, 1993

(87) PCT Pub. No.: WO92/12730

PCT Pub. Date: Aug. 6, 1992

(30) Foreign Application Priority Data

Jan. 17, 1991  (SE) ................................... 9100142

(51) Int. Cl.$^7$ ................................................ A61K 39/00
(52) U.S. Cl. ............................... 424/140.1; 604/4; 604/5; 604/28
(58) Field of Search ................. 604/4; 424/94, 424/130.1, 140.1; 514/2, 21; 435/283, 267

(56) References Cited

U.S. PATENT DOCUMENTS

| | | | |
|---|---|---|---|
| 4,215,688 | 8/1980 | Terman et al. | 604/6.04 |
| 4,223,672 | 9/1980 | Terman et al. | 604/6.06 |
| 4,350,156 | 9/1982 | Malchesky et al. | 604/6.04 |
| 4,371,515 | 2/1983 | Chu | 436/544 |
| 4,375,414 | 3/1983 | Strahilevitz | 210/638 |
| 4,551,435 | 11/1985 | Liberti et al. | 436/541 |
| 4,576,928 * | 3/1986 | Tani et al. | 502/404 |
| 4,687,808 | 8/1987 | Jarrett et al. | 525/54.1 |
| 4,800,016 | 1/1989 | Yang | 210/206 |
| 4,820,261 * | 4/1989 | Schmoll et al. | 604/4 |
| 4,824,432 | 4/1989 | Sturkovich et al. | 604/5.02 |
| 4,846,786 | 7/1989 | Freed et al. | 604/5.01 |
| 4,863,713 | 9/1989 | Goodwin et al. | 424/1.57 |
| 4,865,841 | 9/1989 | Balint et al. | 424/140.1 |
| 4,877,599 | 10/1989 | Lees | 424/1.53 |
| 4,885,207 * | 12/1989 | Johnson et al. | 428/403 |
| 5,069,662 * | 12/1991 | Bodden | 604/4 |
| 5,122,112 * | 6/1992 | Jones | 604/4 |
| 5,149,425 | 9/1992 | Mazid | 210/198.2 |
| 5,252,466 * | 10/1993 | Cronan, Jr. | 435/69.7 |
| 5,474,772 * | 12/1995 | Maddock | 424/140.1 |

FOREIGN PATENT DOCUMENTS

| | | |
|---|---|---|
| 0 132 534 | 5/1984 | (EP) . |
| 2-0 110 409 | 6/1984 | (EP) . |
| WO 88/06045 | 8/1988 | (WO) . |
| WO 90/07929 | 7/1990 | (WO) . |
| WO 91/01749 | 2/1991 | (WO) . |

OTHER PUBLICATIONS

"Activation of prodrugs by antibody–enzyme conjugates: a new approach to cancer therapy", *Faseb Journal* 4 (1990) pp. 188–193.
Wahl et al., J. Nuc. Med., 28:715 (1987).
Strand et al., Abstract Med. Phys., 16(3):465 (1989).
Norrgren et al., Proceeds from 3rd Conference 4:54 (1990).
Ferrone et al., Proceeds from 3rd Conference 4:15 (1990).
Wahl et al., Proceeds from 3rd Conference 4:15 (1990).
Henry et al., Proceeds from 3rd Conference 4:22 (1990).
Nilsson et al., Clin. Exp. Immunol., 82:440 (1990).
Henry et al., Nucl. Med. Biol. 18(5):565 (1991).
Wahl et al.,Nucl. Med. Biol. 15(6):611 (1988).
Ingvar et al., J. Nucl. Med., 30:1224 (1989).
Norrgren et al., Antibody Immunoconj. & Radiopharm., 5(1):61 (1992).

* cited by examiner

*Primary Examiner*—Jean C. Witz
(74) *Attorney, Agent, or Firm*—Swanson & Bratschun L

(57) ABSTRACT

A method and a system is described for reducing non-target levels of specific molecules intended for diagnostic and/or therapeutic applications to vertebrate hosts, wherein said molecules are administered to a vertebrate host and kept therein for a certain time in order to be concentrate to the target by being attached thereto. The molecules which are not attached to the target are removed from the blood circulation system or at least reduced to a lower concentration by passing the blood through an extra-corporeal device.

3 Claims, 2 Drawing Sheets

Figure 1:
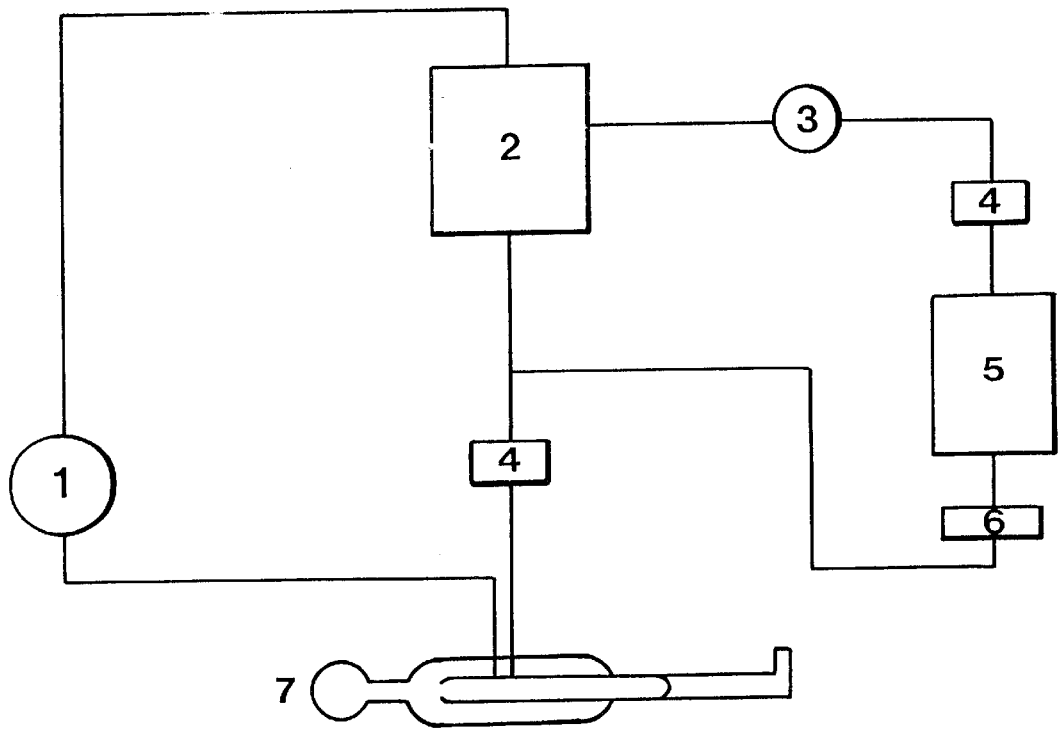

FIG.3A
FIG.3B
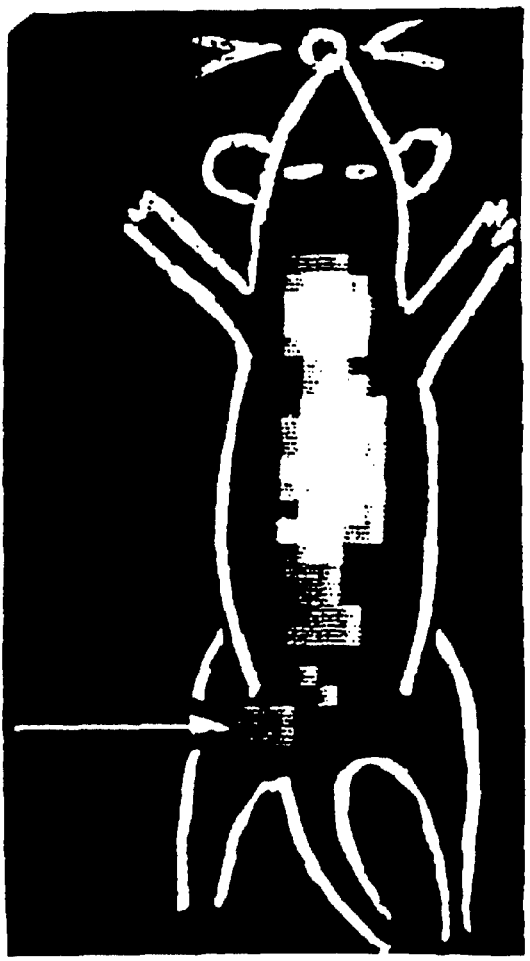
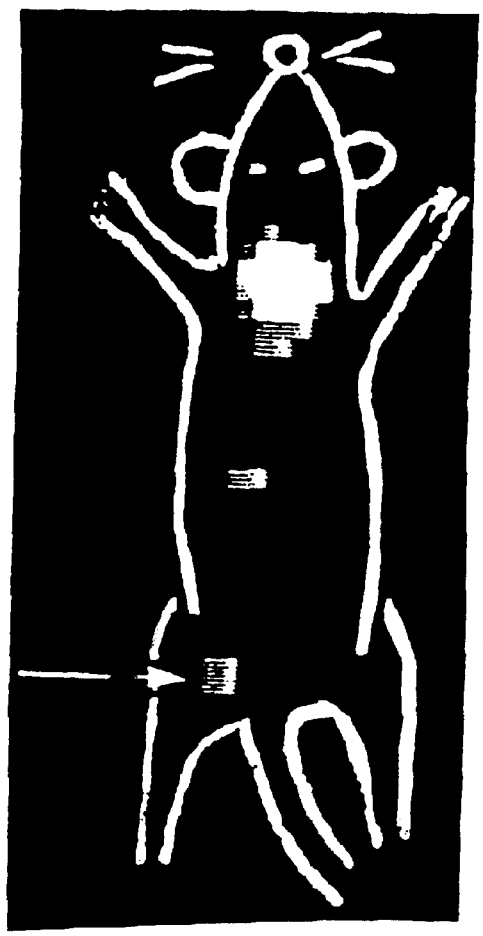

METHOD AND A SYSTEM FOR ENHANCED IN VIVO CLEARANCE OF DIAGNOSTIC AND/OR THERAPEUTIC AGENTS BY EXTRACORPOREAL DEPLETION, AND THE USE OF SAID AGENTS FOR SAID PURPOSE

DESCRIPTION

The present invention relates to a method and a system for reducing non-target levels of specific molecules intended for diagnostic and/or therapeutic applications to vertebrate hosts. In particular, it relates to methods, compositions and means for the extracorporeal removal from the blood circulation of exogenous targeting molecules pre-labelled with a specific affinity ligand which can bind with high affinity to a corresponding receptor immobilized to an extracorporeal device.

The invention is applicable in the removal of any type of exogenous targeting molecule from the blood circulation, provided that these agents are targeted to a specific type of tissue, a specific type of cell or a specific type of extracellular or intracellular marker, and provided that this targeting molecule can be labelled with an affinity ligand without severely affecting the intrinsic affinity and specificity of the targeting molecule. A second requirement is the availability of a receptor to which the affinity ligand has a high affinity, and which in its immobilized form could be used to eliminate the targeting molecule from the blood circulation without affecting endogenous blood components or other exogenous administered components.

Antibodies have been found useful as targeting vehicles for diagnostic and therapeutic agents, inter alia radioisotopes, magnetic resonance imaging agents, enzymes, toxins and cytotoxic drugs or prodrugs. These have been used especially in diagnosis or treatment of cancer. Commonly, antibodies conjugated to diagnostic or therapeutic agents have been administered systemically, but other modes of administration have also been used.

In general, present immunotherapeutic strategies involve the administration of exogenous (non-human) antibodies to the patient These antibodies art intended to interact only with a specific subset of cells while leaving the other cells unaffected. The antibodies are usually conjugated to a lethal agent such as cytotoxic drugs or radioactive isotopes. In these cases, the therapeutic principle will be based entirely on the effect of the exogenously added therapeutic agent. Antibodies can also alone trigger a cytotoxic effect on cells exposing antigens to which the antibodies bind specifically. This is likely to be caused by two different but immunologically related mechanisms. One of these mechanisms, the antibody-dependent cell-mediated cytotoxicity (ADCC), acts through activation of cytotoxic lymphocytes. In the second case, cell lysis is dependent on complement activation which is triggered by antibodies bound to the specific cells. The conceptual simplicity of localizing tumours with radiolabelled antibodies in conjunction with external imaging has led to a great deal of research activity over the past years. Although techniques have improved, the clinical results are still hampered by some major limitations. Several of these limitations are due to parameters which are patient-dependent and can clearly not be altered.

The most important single determinant of detection sensitivity is, nevertheless, the uptake ratio of the localizing antibody on the tumour compared with the same antibody on surrounding normal tissues. Consequently, most work has centered on attempts to improve this uptake ratio with, as yet, limited success. Earlier work in this field has been based on polyclonal antibodies. The development of monoclonal antibodies would seem to have created ideal probes for these attempts. Monoclonal antibodies can be raised to tumour-selective antigens and because of the extremely high specificity there would be very little cross-reactivity with other cell markers, and consequently no, or very little, interaction with cells lacking these markets. However, human studies using mostly mouse monoclonal antibodies have, by and large, been disappointing in that respect. The extreme specificity of monoclonal antibodies, particularly if these antibodies recognize only one epitope per antigen might in some cases lead to a disadvantage in so far that a too small quantity of antibodies will be bound to the target cells, particularly if the number of accessible antigens is small. Mouse monoclonal antibodies might also, in spite of their intrinsic specificity, produce falsely positive localization due to their interaction with human Fc receptors on non-target cells. To overcome these problems, attempts have been made to use immunological fragments derived from monoclonal antibodies. Apart from the fact that these fragments most often lack the ability to interact with cells by non-idiotypic binding, they should also gain access to the target cells more readily than the intact molecule. Smaller molecules like Fab and F(ab)$_2$ fragments do indeed penetrate more rapidly into the tumour (Matzku et al., Int. J. Cancer Suppl. 2, 1988. 11). However, the driving force causing a favourable diffusion of labelled antibodies into tumours is mainly dependent on the concentration gradient (Weinstein et al., Ann. N.Y. Acad. Sci., 1988, 199). Consequently, the blood concentration over time might be more important than the molecular size. Although the uptake of antibody fragment into the tumour might be higher, there is also likely to be a faster secretion of the antibody moieties into the urine. This is supported by data showing that the tumour concentration of antibodies was higher using intact antibody than using the corresponding antibody fragments (Wilbanks et al., Cancer 48, 1981, 1768).

Another approach has been the subtraction of background activity by simultaneous injection of non-target specific antibodies, carrying a second isotope. The latter should mimic the non-specific distribution of the tumour-directed antibody but emits a different photon energy. The two images are then subtracted. Although, this technique should in theory improve the contrast, there are, however, several practical problems. According to Bradwell et al. (Immunology Today 6, 1985, 163) artifacts may result from differences in energy between the two isotopes leading to positioning variability and different tissue attenuation of the gamma rays. Secondly, if the in vivo characteristics of the two isotopes are dissimilar, there will be a differential organ accumulation of the two detached isotopes. For example, the bladder always contains an excess of free iodine or technetium which leads to hot or cold areas. Inequalities may also occur around the heart or stomach. Thirdly, the process of subtraction, while improving contrast, introduces additional statistic fluctuations without increasing the signal. A further disadvantage of this method is that the enhancement of contrast is achieved at the expense of introducing additional radioactive material into the body.

Methods have also been described to enhance the clearance of residual circulating antibodies from the blood circulation. It has been suggested that this could be achieved either by the administration of a second antibody or by modification of the carbohydrate part of the antibody or the antibody conjugate to enhance clearance by hepatic cells. In the former approach, a second antibody which specifically binds to the primary imaging antibody is administered. The second antibody is injected into the patient after sufficient time has elapsed following injection of the primary antibody. The time difference should permit maximum selective uptake of the primary antibody in the tumour to be imaged or treated therapeutically. The second antibodies will form aggregates with unbound imaging antibodies and these aggregates will then be cleared from the blood circulation of the patient through the body's own reticuloendothelial system. There are, however, conflicting views among experts in the field whether this is a feasible method or not (A. Klausner, Biotechnology, 5, 1987,533). Such a method would for example mask several vital organs like spleen, lung, kidney and liver, since these are the organs mainly responsible for the uptake and clearance of the artificially induced immune complexes, referred to as aggregates. It should be noted that even if the primary tumour is not associated with the liver, this organ is nevertheless highly susceptible to metastasis. One also has to consider the risk of fluid phase complement activation caused by a relatively large amount of circulating immune complexes, which could theoretically lead to passive serum sickness. From a therapeutic point of view, one has to worry about the possible damage the conjugated toxins or radioisotope might do to the cells of the spleen and other organs talking care of the "toxic waste". It is likely that these cells over a limited period of time will be exposed to irradiation or toxins of a magnitude close to the maximal tolerable dose of these sensitive organs. Alternative avenues to manipulate the blood clearance rate have recently been presented by M. J. Mattes, J. Natl. Cancer Inst. 79, 1987, 855. Contrary to the method of secondary antibody, this method of blood clearance utilizes the hepatocytes rather than the reticuloendothelial system. According to the latter method enhanced blood clearance can be induced either by better exposing glycoside residues normally associated with the antibodies or by introducing such residues on the antibodies or antibody conjugates through synthetic means. Some of these glycosides will bind tightly to lectin residues exposed on normal hepatic cells, and provided the number of such residues are sufficiently high, the antibodies or antibody conjugates will be accumulated in the liver and thereby cleared from the blood circulation. Radiolocalization studies have shown that target/non-target radioactivity ratios may be significantly improved by introducing a two stage system in which radiolabelled avidin is administered following the injection of a biotinylated antibody (Paganelli, G. et al., Int. J. Cancer. Suppl. 2, 1988, 121; Oehr, P. et al. J. Nuclear. Med. 29, 1988, 728), or, alternatively, if radiolabelled biotin is injected following the administration of avidin-antibody conjugates (Hnatowich, D.D. et al. J. Nuclear Med. 28, 1987, 1294). In general, these methods would suffer from drawbacks similar to those of the second antibody approach. The liver will be the recipient of the toxic waste and this vital organ will be masked for imaging. Furthermore, it should be difficult to use this method successfully if an antibody accumulation in the target site is orders of magnitude slower than accumulation in the liver. This method would also require a great deal of enzymatic or organic synthetic manipulation on the active component i.e. the antibody conjugate.

Specific removal of antibodies from the blood circulation by extracorporeal means is commonly applied in the therapy of immune-related disorders. The first attempt to remove endogenous antibodies from blood by employing hemoperfusion through a porous gel was described by Schenkein et al. in 1971 (Schenkein et al. J. Clin. Invest. 50, 1971, 1864). Somewhat later, Terman and co-workers (Lancet 2, 1979, 824) presented a technique in which a patient suffering from systemic lupus erythematosus was successfully treated by passing the patients plasma through a collodion-charcoal device. Extracorporeal techniques have also been used to overcome blood-group incompatibility. Blood treatment systems for the removal of anti-A and anti-B antibodies utilizing a technique in which synthetic blood-group antigens are covalently linked to a matrix have been described (Bensinger et al. N. Engl. J. Med. 304, 1981, 160). Protein A covalently linked to a sepharose matrix has been used with the purpose to remove immunoglobulins from the blood-circulation in patients suffering from autoimmune diseases or from hyperimmunized patients. The principle outline of such a system has been presented (Larsson, L. Å. et al, In Progress in Artificial Organs; Nosey, Kjellstrand, Ivanovich, eds., Cleveland, ISAO Press 1985, p902). Systems based on this principle have been used to reduce the level of anti-HLA antibodies prior to kidney transplantation of hyperimmunized patients (Palmer, A. et al., Lancet i, 1989, 10), and to remove anti-FVIII or anti-FIX antibodies to enable a successful treatment of heamophilia patients with factor extracts (Nilsson, I. M. et al., Blood 52, 1981, 38).

A system for the extracorporeal adsorption of immunoglobulins and circulating immune complexes utilizing columns where protein A has been covalently linked to a silica matrix is descibed in U.S. Pat. No. 4,681,870. The extracorporeal removal of endogenous antibodies produced in response to treatment with exogenous antibody have been presented in the European Patent Application No. 88309909.5. Removal of specific antibodies from whole blood in a continuous extracorporeal system has also been described (Nilsson, I.M. et al., Plasma Ther. Transfus. Technol. 5, 1984, 127).

A DIAGNOSTIC CONCEPT

This innovation can be utilized for diagnostic purposes in different ways. It can, for instance, be used with immunoscintigraphy for detection/localization of residual tumour growth and the presence of metastases. Another principle application is named immuno-guided surgery, where it can be used to better locate and define the borderline between tumour and normal tissues at the surgical procedure.

In the following general description of the techniques, the tumour targeting molecule is exemplified by monoclonal antibodies and the extracorporeal adsorbent by avidin-columns.

The technology is based on increased uptake of radioactivity in tumour tissue compared to normal tissues. The radioactivity is selectively targeted to the tumour by using molecules specific for tumour antigens e.g. monoclonal antibodies. The distribution of radioactivity in the body is imaged by a scintillation camera.

The procedure involves the following steps:

ADMINISTRATION OF RADIOLABELLED IMMUNOCONJUGATE

Tumour-selective monoclonal antibodies, labelled with a gamma-emitting radionuclide and conjugated with biotin, are injected into the patient The immunoconjugate will distribute throughout the body and selectively target to areas with tumour growth.

DEPLETION OF CIRCULATING IMMUNOCONJUGATE

After a certain time, normally one to two days after the injection of the immunoconjugate, the uptake in the tumour has usually reached a maximum. However, only a small portion of the injected activity is localized to the tumour and most of the immunoconjugate is distributed in the circulation and the normal tissues. This excess of immunoconjugate increases the background and should be removed in order to improve the immunoscintigraphy. The depletion is performed by extracorporeal immunoadsorption of plasma through an avidin-column. Blood is drawn from the patient and continuously passed through a plasma separation device i.e. a plasma filter or an online centrifuge, the plasma is then passed through an avidin-adsorbent and the depleted plasma is mixed with the blood and returned to the patient. By this procedure about 90–95% of the immunoconjugate, i.e. the targeting molecule carring the affinity ligand, is removed from the blood circulation after processing of about three times the plasma volume. The invention includes, however, also the possibility that the immunoconjugate is removed directly from whole blood.

DETECTION OF RADIOACTIVITY

IMMUNOSCINTIGRAPHY

After termination of the extracorporeal treatment, the patient is placed in front of a scintillation camera and the distribution of radioactivity in the body is imaged with either planar or tomografic techniques. The tumour-to-background ratio in the images is improved. The immunoscintigraphic analysis may be repeated on day one or two.

IMMUNO-GUIDED SURGERY

Following termination of the extracorporeal procedure, the patient is ready for surgery. During surgery, the borderline between tumour and normal tissues is defined by the use of a hand-operated radioactivity detection probe.

A THERAPEUTIC CONCEPT

The basis for this therapy is that tumour-selective agents e.g. monoclonal anti-bodies are used for selective targeting of tumour killing or tumour retarding substances to the tumour. The anti-tumour agent might incorporate radionuclides, toxins, cytostatics, enzymes that activate prodrugs, or other suitable drugs linked to the antibodies. However, many of these agents might at higher concentration have cytotoxic or cystostatic effects on normal cells resulting in undesirable side effects in the patient. Even in the case of a highly tumour-selective targeting molecule (e.g. monoclonal antibody), only a small portion of the substance will be localized to the tumours. The remaining will be present in the blood circulation and in normal tissues. The innovation described in this patent application can be utilized for elimination of the circulating toxic substances from the blood, resulting in decreased side effects on normal tissues.

The immunoconjugates to be used in connection with this innovation consist of three principal parts; a tumour-targeting module (e.g. a monoclonal antibody), an anti-tumour module (e.g. radionuclides, drugs etc), and an affinity ligand (e.g. biotin). The conjugate can be removed by utilizing the biospecific interaction with the affinty ligand (e.g. an avidin-adsorbent). Two or all three said functions may, however, be provided by one and the same molecule.

The procedure involves the following steps:

ADMINISTRATION OF THERAPEUTIC IMMUNOCONJUGATE

Tumour-selective monoclonal antibodies, conjugated with an anti-tumour agent, and labelled with preferably biotin, are administered to the patient. The immunoconjugate will distribute throughout the body and selectively target to areas with tumour growth.

DEPLETION OF CIRCULATING IMMUNOCONJUGATE

After a certain time, normally one to two days after the injection of the immunoconjugate, the uptake in the tumour has reached a maximum. However, only a small portion of the injected dose is localized to the tumour and most of the immunoconjugate is distributed in the circulation and normal tissues. This excess of immunoconjugate increases the risk of side effects and has to be removed in order to improve the therapy. The depletion is performed by extracorporeal immunoadsorption of plasma, preferably by utilizing an avidin column. Blood is drawn from the patient and continuously passed through a plasma separation device i.e. plasma filter or online centrifuge. The plasma is then passed through an avidin adsorbent and the depleted plasma is mixed with the blood and returned to the patient. By this procedure about 90–95% of the immunoconjugate, present in the blood, is removed after processing of about three times the plasma volume. The invention includes, however, also the possibility that the immunoconjugate is removed directly from whole blood.

The injection of immunoconjugate and the subsequent removal of the excess of this toxic conjugate from the circulation may have to be repeated dependent on the nature of the neoplastic disease.

EMBODIMENTS

The method of the present invention relies on the specific removal of previously administered synthetically modified target-specific agents from the blood circulation in a host to be treated. Removal of these targeting molecules is achieved by the use of a specific adsorbent device having immobilized receptors specific to the affinity ligand. The latter may be covalently bound to the original targeting molecule. Such targeting molecules may constitute proteins, carbohydrates or polynucleotides or may contain parts of these structural elements. Among proteins are the antibodies which could be of different isotypes and could originate from any species. Of particular interest are the monoclonal antibodies and derivatives thereof. The latter include enzymatically produced fragments such as the F(ab')$_2$, F(ab'), F(ab) and the like. They also include genetically engineered hybrids or chemically synthesized peptides based on the specificity of the antigen binding region of one or several target specific monoclonal antibodies e.g. chimeric antibodies, single chain antibodies etc.

The present invention may rely on the ability of covalent attachment of a specific affinity ligand onto the targeting molecule in a manner that does not severely affect the affinity and/or specificity of the targeting molecule in its interaction with the desired target cell. The affinity ligand may be any molecule which can be covalently attached to the targeting molecule. For therapeutic purposes the affinity ligand and the cytotoxic agent may constitute one single molecule to be attached to the targeting macromolecule. Cytotoxic agents, such as radionuclides, drugs or prodrugs may also be introduced directly on to the affinity ligand before or after attaching the affinity ligand to the targeting molecule. The affinity ligand may also be a prodrug. Furthermore, the affinity ligand may in addition also serve as an activator of prodrugs. In that case, the activator (e.g. an enzyme) being linked to the targeting molecule, may convert a prodrug to an active drug or toxin on (or close to) the target site (Senter, P. D. FASEB J. 4,188, 1990). For the application of in vivo diagnosis, the targeting molecule should carry an imaging agent, such as a radioisotope or a magnetic resonance imaging agent. These could be introduced directly onto the targeting molecule or the affinity ligand or the conjugate of the two. Although the affinity ligand may vary, biotin or derivatives thereof, e.g. 2-iminobiotin, desthiobiotin, diaminobiotin, would fulfill most of the requirements for this application. Biotin has an exceptionally high affinity for its receptor i.e. avidin or streptavidin. Biotin is easily coupled to antibodies often without loss of binding capacity. The biotin-avidin complex has a very small dissociation rate constant leading to an extremely long half life of the complex.

Biotinylation of proteins such as immunoglobulins can be achieved through various means. The amino groups in proteins can easily be conjugated by the use of biotinyl-p-nitrophenyl esters or biotinyl-N-succinimide esters. The coupling can also be achieved by direct coupling with carbodiimide, particularly water soluble derivatives of the latter. In some cases it may be an advantage to use spacers of various length like caproylamidobiotinyl esters. Alternative ways of preparing biotin derivatives active with groups other than amino groups are also commonly used. Among these are biotinyl hydrazide which reacts with sugar and nucleic acid residues and biotinyl-bromoacetyl hydrazide or biotin maleimide which reacts with sulfhydryls and other strong nucleophiles. Biotinyl-diazoanilide can be used to conjugate biotin to phenol or imidazole functions. There are also other means by which the carboxyl group of the valeric acid side chain can be activated or converted to a reactive function.

The receptor to which the affinity ligand has a high affinity may be immobilized to various types of solid supports. The coupling method of choice will depend on the nature of the receptor as well as the nature of the immunosorbent support matrix. For protein based receptors, functional groups such as hydoxyl-, amino- , carboxyl- or thiol-groups may be utilized. Glycoproteins may be coupled to the matrix via their glycoresidues. The solid support may also be activated to enable binding of the receptor by means in which the receptor forms linkages with the solid support through specific or non-specific reaction with the side-chains or the backbone structure of the receptor protein. The linkage between the solid support and the receptor may also be of non-covalent nature, where electrostatic or hydrophobic forces are utilized. Apart from the biotin/avidin system other combinations of affinity ligand and corresponding receptors can be used within the scope of this invention. The following list is by no means complete and will merely serve as examples of additional combinations of affinity ligands and their receptors.

Antibody/antigen (haptens)

e.g. anti-DNP antibodies/targeting molecules conjugated with DNP.

Lectins/saccharide residues e.g. lectin from Sambueus nigra/beta-D-gal(1–4)-D-glc Enzyme/enzyme inhibitors e.g. D-Alanin carboxypeptidase from B.subtilis or E.coli/ 6-amninopenicillanic acid or p-aminobenzylpenicillin.

e.g. Dehydrofolate reductase/aminopterin or amethopterin

Protein/co-factors.

e.g. Intrinsic factor/vitamin B12 or cobalamin.

The adsorbent device to which the receptor is immobilized may be of various shapes and chemical compositions. It may for example constitute a column house filled with particulate polymers, the latter of natural origin or artificially made. The particles may be macroporous or their surface may be grafted, the latter in order to enlarge the surface area. The particles may be spherical or granulated and be based on polysaccharides, ceramic material, glass, silica, plastic, or any combination of these or a like material. A combination of these could for example be solid particles coated with a suitable polymer of natural origin or artificially made. Artificial membranes may also be used. These may be flat sheet membranes made of cellulose, polyamide, polysulfone, polypropen or other types of material which are sufficiently inert, biocompatible, non-toxic and to which the receptor could be immobilized either directly or after chemical modification of the membrane surface. Capillary membranes like the hollow fibers made from cellulose, polypropen or other materials suitable for this type of membranes may also be used.

The principle outline of a system for processing of human plasma with the aim of removing exogenous targeting molecules in accordance with the invention is described in FIG. 1 . Blood is drawn from the patient through a peristaltic pump (1) at a flow of typically 20–50 ml per min. The blood is separated into plasma and blood cells in a standard blood separation device (2), either through centrifugation or by the use of a plasma filter. Heparin and/or citrate may be added to the blood prior to the plasma separation in order to prevent blood coagulation and reduce complement activation.

Prior to entering the adsorbent device (5), the plasma flow will be monitored with respect to pressure and air bubbles. The latter will be removed in a standard air-trap. An optional safety filter device (6) may be used to remove any debris or particles coming out from the adsorbent device. The plasma will finally mix with the patients own blood cells and the blood will pass a second air-trap (4) and the pressure will be monitored before the blood is returned to the patient. A similar extracorporeal plasma adsorption system for removal of immune complexes has been described (Wallmark, A. et al., Artificial Organ 8, 1984, 72).

Figure 2:
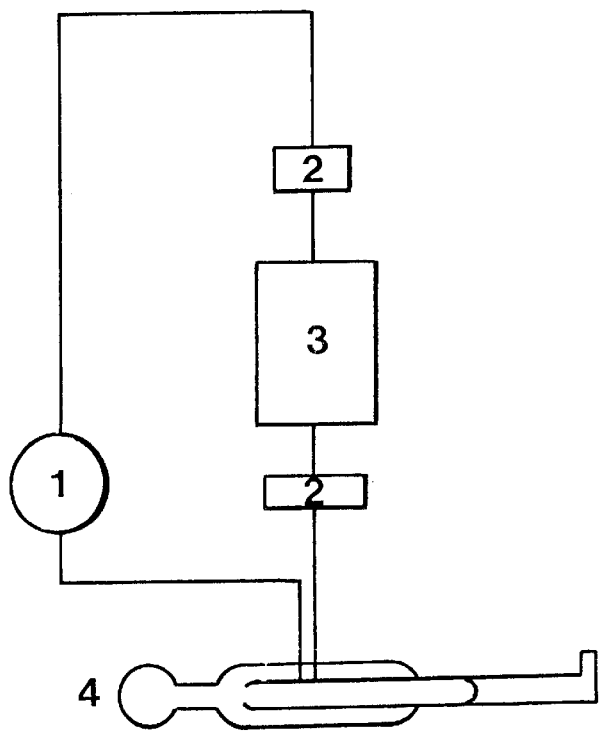

The procedure is greatly simplified if whole blood rather than plasma is processed. The princple outline of such a system is shown in FIG. 2. Removal of specific antibodies in a continous extracorporeal whole blood system has previously been described (Nilsson , I. M et al., Plasma Ther. Transfus. Technol. 5, 1984, 127).

The following experiments are far from optimized, and should merely serve as an illustration of the use of the invention, and are not limitative of the remainder of the disclosure in any way whatsoever.

EXPERIMENTAL

Material and Methods

1. The Animal Model

Nude rats with thymic aplasia have become generally accepted for testing of monoclonal antibodies for immunoscintigraphy and immunotherapy. With the possibility of implanting human tumour material in these rats, experimental animals are obtained which express human tumour antigens, in a defined place. We utilized nude rats (Rowett RNu/RNu strain) transplanted with tumour cells obtained from a tumour biopsy from a patient with melanoma metastases. The monoclonal antibody was the 96.5 (mouse IgG2a) specific for p97, a cell surface glycoprotein with the molecular weight of 97,000 present on 60–80% of human melanoma. The tumour model has been described in detail (Ingvar. C. et al. Nucl. Med 30. 1989, 1224).

2. Conjugation and Labelling of Monoclonal Antibodies

The monoclonal antibody 96.5 (330 ug) was labelled with 37 MBq iodine-125 ($^{125}$I), using the Chloramine-T method. By elution on a Sephadex G25 column (Pharmacia PD10) the fraction containing the labelled protein was collected and used for the conjugation. The labelling efficiency of the $^{125}$I 96.5 was around 70%. The radiolabelled monoclonal antibody was conjugated with biotin by mixing 500 ug of antibody with 41 ug of N-Hydroxysuccinimido-biotin (NHS-biotin) in 0.1M $NaHCO_3$, 0.15M NaCl with 10% DMSO. The mixture was incubated for 1 h at room temperature, followed by overnight incubation at 4° C. The $^{125}$-McAb-biotin conjugate was separated from free biotin-reagent by gelfiltration on a Sephadex G25 column, equilibrated with PBS (10 mM Sodium phosphate, 0.15 M NaCl, pH 7.3). The conjugate was stored at 4° C until used.

3. Radioimmunoscintigraphy with Extracorporeal Immunoadsorption of Plasma

Nude rats (Rowett RNu/RNu strain), 2–3 months of age, with a weight of 210+25 g were used. The rats were transplanted with tumour cells, established from a human melanoma metastase, on each thigh: intramuscularly (left) and subcutaneously (right). The immunoconjugate was injected 1–2 weeks after tumour inoculation when the tumour was just palpable. Four to seven days before injection of immunoconjugate, the rats to be treated with extracorporeal immunoadsorption have been catheterized using the carotid and the jugular blood vessels. 24 hours after injection of 50 µg conjugate (3 MBq), the rats were treated with extracorporeal immunoadsorption. Blood was pumped continuously through a hollow-fiber plasmafilter at a rate of 1.5 ml/min and plasma was separated and passed through an adsorbent column at a flow rate of 0.2 ml/min. The column contained 1.2 ml of avidin-sepharose, highly specific for adsorption of the biotin-conjugate. Approximately three plasma volumes were treated during a 3 h period. The animals were imaged with a scintillation camera (General Electric T400) before, and directly after the extracorporeal treatment. The rats were killed with an overdose of ether and various organs (see Table 1 for list of organs) were removed. Each tissue sample was weighed and measured in an automatic NaI(T1) gamma counter for radioactivity content. The specific tissue uptake was expressed as % of injected dose per gram of tissue (%/g) and as an uptake ratio (%/g tumour)/(%/g tissue). Control rats were neither catheterized nor treated with extracorporeal immunoadsorption.

Results

During extracorporeal immunoadsorption of these rats, 90–95% of the radioactivity in the blood was removed, corresponding to about 40–50% of the total activity in the animals. The immunoscintigrams are presented in FIG. 3, and the results from the measurements of tissue specific activities in Table 1. These results are well in agreement with theoretical evaluations based on simulated extracorporeal immunoadsorption using a computerized mathematical model.

3. Radioimmunoscintigraphy with Extracorporeal Immunoadsorption of Whole Blood

Euthymic rats (Wistar/Furth strain), 2–3 months of age, with a weight of 210±25 g were used. Four to seven days before injection of immunoconjugate, the rats were catheterized using the carotid and the jugular blood vessels. 24 hours after injection of 50 µg conjugate (5 MBq), the rats were subjected to extracorporeal immunoadsorption. Blood was pumped continuously through an adsorbent column at a flow rate of 0.2 ml/min. The column (1.5 ml) contained avidin covalently linked to Sepharose 6 MB macrobeads. The macrobeads allow direct adsorption of whole blood. Approximately three blood volumes were treated during a 3 h period. The animals were analyzed with a scintillation camera (General Electric T400) before, and directly after the extracorporeal treatment. The rats were killed with an overdose of ether and various organs (see Table 2 for list of organs) were removed. Each tissue sample was weighed and measured in an automatic NaI(T1) gamma counter for radioactivity content. The specific tissue uptake was expressed as % of injected dose per gram of tissue (%/g). Control rats were neither catheterized nor treated with extracorporeal immunoadsorption.

Results

During extracorporeal immunoadsorption of the rats, 90–95% of the radioactivity in the blood was removed corresponding to about 40–50% of the total body activity. The immunoscintigrams are presented in FIG. 3, and the results from the measurements of tissue activities in Table 2. The extracorporeal immunoadsorption of whole blood was of the same efficiency as immunoadsorption of plasma, but is technically easier to perform.

The invention is of course not restricted to the above described examples, but may be varied within the scope of the following claims. The specific molecules may for instance be removed by other means than adsorption. Alternative methods may be filtration and/or centrifugation.

TABLE 1

Tissue uptake and binding ratio with and without extracorporeal immunoadsorption.

| Tissue | Control Rats %/gram | Control Rats ratio | Rats treated with ECIA %/gram | Rats treated with ECIA ratio | % depletion | improvement |
|---|---|---|---|---|---|---|
| Tumour | 0.48 ± 0.03 | 1.00 | 0.24 ± 0.11 | 1.00 | 50.1 | 1.00 |
| plasma | 2.23 ± 0.37 | 0.22 ± 0.06 | 0.15 ± 0.03 | 1.34 ± 0.64 | 93.1 | 5.99 |
| Lymph nodes | 0.38 ± 0.07 | 1.30 ± 0.32 | 0.18 ± 0.08 | 1.29 ± 0.27 | 51.9 | 0.99 |
| muscules | 0.17 ± 0.09 | 3.35 ± 1.45 | 0.10 ± 0.02 | 2.50 ± 0.89 | 43.7 | 0.75 |
| kidney | 0.35 ± 0.05 | 1.39 ± 0.25 | 0.07 ± 0.02 | 3.86 ± 2.21 | 80.8 | 2.78 |
| liver | 0.32 ± 0.05 | 1.52 ± 0.19 | 0.05 ± 0.02 | 5.24 ± 3.69 | 83.9 | 3.45 |
| spleen | 0.23 ± 0.03 | 2.17 ± 0.33 | 0.04 ± 0.006 | 6.95 ± 4.35 | 83.5 | 3.20 |
| heart | 0.22 ± 0.08 | 2.45 ± 1.03 | 0.07 ± 0.01 | 3.37 ± 1.34 | 67.9 | 1.37 |
| lung | 0.52 ± 0.07 | 0.95 ± 0.15 | 0.14 ± 0.07 | 1.70 ± 0.43 | 72.1 | 1.80 |
| bone marrow | 0.34 ± 0.05 | 1.44 ± 0.24 | 0.05 ± 0.01 | 5.47 ± 3.02 | 86.4 | 3.79 |
| stomach | 0.22 ± 0.003 | 2.05 ± 0.08 | 0.17 ± 0.09 | 1.62 ± 1.52 | 24.3 | 0.79 |

%/gram: % of the total body activity measured per gram of the respective tissue. (mean ± S.D.)
Ratio: (%/gram tumour)/(%/gram normal tissue) (mean ± S.D.)
ECIA: extracorporeal immunoadsorption.
% depletion: 100*((%/gram without ECIA- %/gram with ECIA)/(%/gram without ECIA))
Improvement: ratio with ECIA/ratio without ECIA.

TABLE 2

Tissue uptake and binding ratio with and without extracorporeal immunoadsorption of whole blood.

| Tissue | Control Rats %/gram | Rats treated with ECIA %/gram | % depletion |
|---|---|---|---|
| plasma | 3.22 | 0.35 | 89.1 |
| lymph nodes | 0.31 | 0.25 | 19.4 |
| muscules | 0.11 | 0.08 | 27.3 |
| kidney | 0.56 | 0.11 | 80.4 |
| liver | 0.42 | 0.10 | 76.2 |
| spleen | 0.24 | 0.09 | 62.5 |
| heart | 0.35 | 0.13 | 62.8 |
| lung | 0.60 | 0.24 | 60.0 |
| bone marrow | 0.45 | 0.13 | 71.1 |

%/gram: % of the total body activity measured per gram of the respective tissue. (mean)
ECIA: extracorporeal immunoadsorption of whole blood.
% depletion: 100*((%/gram without ECIA- %/gram with ECIA)/(%/gram without ECIA))

What is claimed is:

1. A method for reducing levels of non-tissue-bound conjugates or single molecules, said conjugates comprising antibodies or derivatives thereof that are each covalently attached to a single molecule comprising a biotin or avidin and a radiolabel, said antibodies or fragments being selective for certain tissues or cells, and wherein said conjugates are administered to a vertebrate host and kept therein for a certain time in order to be concentrated to the target tissues or cells by said antibodies or derivatives being attached thereto, wherein the conjugates or single molecules which are not attached to the target tissues or cells are completely or partially removed from the blood circulation by passing the blood or plasma through an adsorption device containing immobilized avidin or biotin, respectively.

2. A system for reducing levels of non-tissue bound conjugates or single molecules, wherein said conjugates comprise antibodies or derivatives hereof that are each covalently attached to a single molecule comprising a biotin or avidin and a radiolabel, said antibodies or derivatives thereof being selective for certain tissues or cells, said conjugates intended for diagnostic or therapeutic applications to vertebrate hosts, including means for adding said conjugates to the blood circulation for keeping them therein for a certain time in order to be concentrated to the target tissues or cells by said targeting molecules being attached thereto, means for extracorporeal circulation of blood or plasma through an a absorption device having immobilized thereto avidin or biotin, respectively, means for removing the conjugates or single molecules which are not attached to the target from the blood or plasma passing through said adsorption device, and means for the return of the blood to the patient from the extracorporeal circulation.

3. A method for diagnosing or treating disease in a vertebrate comprising the steps of:

(a) adding conjugates comprising tissue or cell selective antibodies or derivatives thereof each of which is covalently attached to a single molecule comprising an avidin or biotin molecule and a radiolabel, wherein said avidin or biotin has affinity for an immobilized biotin or avidin, respectively, to the circulatory system of the vertebrate;

(b) maintaining the conjugates in the circulatory system of the vertebrate to concentrate the antibodies to target cells or target tissue; and (c) passing the blood of the vertebrate into an extracorporeal adsorption device comprising the immobilized avidin or biotin, thereby removing the non-tissue bound conjugates or single molecules.

* * * * *